(12) United States Patent
Irisawa et al.

(10) Patent No.: US 9,662,020 B2
(45) Date of Patent: May 30, 2017

(54) PROBE

(71) Applicant: FUJIFILM Corporation, Tokyo (JP)

(72) Inventors: Kaku Irisawa, Ashigarakami-gun (JP); Takeya Abe, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 344 days.

(21) Appl. No.: 14/449,500

(22) Filed: Aug. 1, 2014

(65) Prior Publication Data
US 2014/0343394 A1   Nov. 20, 2014

Related U.S. Application Data

(63) Continuation of application No. PCT/JP2013/000523, filed on Jan. 31, 2013.

(30) Foreign Application Priority Data

Feb. 3, 2012   (JP) ................................ 2012-021670
Jan. 24, 2013  (JP) ................................ 2013-011039

(51) Int. Cl.
*A61B 6/00*     (2006.01)
*A61B 5/00*     (2006.01)

(52) U.S. Cl.
CPC .................. *A61B 5/0095* (2013.01)

(58) Field of Classification Search
CPC .................................................... A61B 5/0095
USPC ................................................. 600/437–480
See application file for complete search history.

(56) References Cited

U.S. PATENT DOCUMENTS

| | | | |
|---|---|---|---|
| 5,345,926 A * | 9/1994 | Chikama | A61B 1/227 600/200 |
| 2010/0229650 A1* | 9/2010 | Shahzad | A61B 5/0059 73/655 |
| 2011/0134656 A1* | 6/2011 | Kitano | A61B 1/00126 362/554 |

(Continued)

FOREIGN PATENT DOCUMENTS

| | | |
|---|---|---|
| JP | 5-220111 A | 8/1993 |
| JP | 7-5376 A  | 1/1995 |

(Continued)

OTHER PUBLICATIONS

International Search Report, issued in PCT/JP2013/000523, dated Apr. 9, 2013.

(Continued)

*Primary Examiner* — Sanjay Cattungal
(74) *Attorney, Agent, or Firm* — Birch, Stewart, Kolasch & Birch, LLP

(57) ABSTRACT

An acoustic wave detector that detects an acoustic wave from a subject, an optical fiber that guides light emitted from a light source to a probe body, and a light guide member that guides light from a light entrance end, which is optically coupled to the optical fiber, to a light exit end, which is located in the vicinity of the acoustic wave detector, are provided. The light guide member is secured in the probe body with a securing material provided at least partially around the light guide member. The conditional expression below is satisfied:

$$\sin^{-1}(n2/n1) \times (180°/\pi) < 90° - \theta i$$

where n1 is a refractive index of the light guide member, n2 is a refractive index of the securing material, and $\theta i$ is a spread angle of incoming light from the optical fiber.

20 Claims, 5 Drawing Sheets

(56) References Cited

U.S. PATENT DOCUMENTS

2013/0310694 A1\* 11/2013 Tsujita ................ A61B 8/4416
600/459

FOREIGN PATENT DOCUMENTS

| JP | 7-313507 A | 12/1995 |
| --- | --- | --- |
| JP | 8-10255 A | 1/1996 |
| JP | 2001-215517 A | 8/2001 |
| JP | 2008-49063 A | 3/2008 |
| JP | 2011-501150 A | 1/2011 |
| JP | 2011-120627 A | 6/2011 |
| WO | WO 2012/108171 A1 | 8/2012 |

OTHER PUBLICATIONS

Written Opinion of the International Searching Authority, issued in PCT/JP2013/000523, dated Apr. 9, 2013.

\* cited by examiner

PROBE

CROSS-REFERENCE TO RELATED APPLICATIONS

This application is a Continuation of PCT International Application No. PCT/JP2013/000523 filed on Jan. 31, 2013, which claims priority under 35 U.S.C §119 (a) to Japanese Patent Application No. 2012-021670 filed on Feb. 3, 2012 and Japanese Patent Application No. 2013-011039 filed on Jan. 24, 2013. Each of the above applications is hereby expressly incorporated by reference, in its entirety, into the present application.

TECHNICAL FIELD

The present invention relates to a probe, and more particularly to a probe used in photoacoustic imaging.

BACKGROUND ART

Ultrasonography is known as one of imaging examination methods that allow non-invasive examination of the state of the interior of a living body. In ultrasonography, an ultrasound probe that can transmit and receive ultrasound is used. Ultrasound transmitted from the ultrasound probe to the subject (living body) travels through the interior of the living body and is reflected at a tissue interface. Then, the reflected ultrasound is received by the ultrasound probe. Based on the time taken for the reflected ultrasound to return to the ultrasound probe, the distance is calculated, thereby imaging the state of the interior.

Further, photoacoustic imaging, which images the interior of a living body using the photoacoustic effect, is known. In photoacoustic imaging, in general, pulsed laser light, for example, is applied to the interior of a living body. In the interior of the living body, a living tissue absorbs energy of the pulsed laser light and ultrasound (a photoacoustic signal) is generated due to adiabatic expansion caused by the energy. This photoacoustic signal is detected using an ultrasound probe, or the like, and a photoacoustic image is constructed based on the detected signal, thereby visualizing the interior of the living body based on the photoacoustic signal.

Usually, in a ultrasound probe, the interior of the probe body is filled with a potting agent to secure parts contained in the probe body. Potting the interior of the probe body is taught, for example, in Japanese Unexamined Patent Publication Nos. 7(1995)-313507 and 8(1996)-010255 (hereinafter, Patent Documents 1 and 2). As the potting agent, an epoxy resin, etc., may be used, for example.

In the photoacoustic imaging, light from a laser light source may be guided to the ultrasound probe using an optical fiber, or the like, to apply the laser light from the ultrasound probe. An ultrasound probe including a light application section is taught in Japanese Unexamined Patent Publication No. 2008-49063 (hereinafter, Patent Document 3), for example. Patent Document 3 teaches that the end portion of the optical fiber on the light exit end side is disposed adjacent to ultrasound transducers and secured integrally with the ultrasound transducers. The light exit end of the optical fiber is secured in a hole provided in a holder such that the light is applied in a direction in which ultrasound from the ultrasound transducers travels.

DISCLOSURE OF INVENTION

As an ultrasound probe including a light application section, an ultrasound probe that includes light guide plates in a probe body, wherein light guided using optical fibers, or the like, is inputted to the light guide plates and the light is outputted toward the subject from light exit faces of the light guide plates, is considered. The light guide plates may be made of quartz glass, for example. The probe body of the above-described ultrasound probe is filled with a resin, such as an epoxy resin, to secure component parts, including the light guide plates, contained in the probe body. At this time, if a commonly-used potting agent is used to secure the light guide plates, there is only a small refractive index difference between the light guide plates and the potting agent and the light in the light guide plates may not be reflected in the light guide plates, causing light leakage.

More specifically, a typical optical fiber has a numerical aperture of NA=0.23, and a spread angle θi of the outgoing light is around 13.3° (θi=sin$^{-1}$(NA)). A standard refractive index of a commonly-used potting agent, such as an epoxy agent, is in the range from 1.42 to 1.45. In the case where the light guide plates are made of quartz, the refractive index of the light guide plates is 1.45 for light having a wavelength in the range from 700 nun to 800 nm. When the light from the optical fiber is normally incident on the light entrance side of each light guide plate having a rectangular solid shape, the light outputted from the optical fiber has the spread angle θi, and the maximum incidence angle of the outgoing light from the optical fiber incident on the interface between the light guide plate and the potting agent is 90°−θi=76.7°.

In a case where the potting agent has a refractive index of 1.42, the critical angle (the smallest incidence angle for total reflection) at the interface between the light guide plate and the potting agent is 78.3°. In a case where the potting agent has a refractive index of 1.45, the critical angle at the interface between the light guide plate and the potting agent is 90°. In these cases, the light from the optical fiber enters the interface between the light guide plate and the potting agent at an angle smaller than the critical angle. Therefore, part of the light travelling through the light guide plate is not reflected at the interface between the light guide plate and the potting agent, causing light leakage.

In view of the above-described circumstances, the present invention is directed to providing a probe that can prevent light leakage from light guide plates that are secured in a probe body with a potting agent.

In order to accomplish the above-described object, the invention provides a probe comprising: an acoustic wave detector that detects at least an acoustic wave from the subject; an optical fiber that guides light emitted from a light source to a probe body; and light guide means that guides light from a light entrance end to a light exit end, the light entrance end being optically coupled to the optical fiber and the light exit end being located in the vicinity of the acoustic wave detector, wherein the light guide means is secured in the probe body with a securing material provided at least partially around the light guide means, and the conditional expression below is satisfied:

$$\sin^{-1}(n2/n1) \times (180°/\pi) < 90° - \theta i$$

where n1 is a refractive index of the light guide means, n2 is a refractive index of the securing material, and θi is a spread angle of light entering the light entrance end from the optical fiber.

In the invention, the light guide means may at least partially be made of glass.

As the securing material, a fluorine resin material may be used. Specifically, tetrafluoroethylene-perfluorodioxole copolymer (TFE/PDD) may be used as the securing material.

Alternatively, a fluorosilicone rubber may be used as the securing material. Still alternatively, a low-refractive index silicone resin or a methyl silicone resin having a refractive index lower than the refractive index of the light guide means may be used as the securing material.

In the invention, the light exit end of the light guide means may be covered with the securing material.

The light guide means may comprise a first light guide member that guides light emitted from the light source, and a second light guide member that diffuses and guides the light guided by the first light guide member to the vicinity of the acoustic wave detector.

In this case, the second light guide member may comprise a light diffusing member that diffuses incoming light, the light diffusing member being disposed on the side where light from the first light guide member enters.

It is preferred that the conditional expression below be satisfied:

$$\sin^{-1}(n2/n3) \times (180°/\pi) < 90° - \theta d \text{ (where } \theta d = (\theta i^2 + \theta 1^2)^{1/2}),$$

where n3 is a refractive index of the second light guide member, and θ1 is a diffusion angle of the light diffusing member.

At least the second light guide member of the first and second light guide members may be secured with the securing material. Alternatively, only the second light guide member of the first and second light guide members may be secured with the securing material.

In the invention, a structure where the securing material is provided to extend over a side surface of the light guide means between the light entrance end and the light exit end may be adopted.

Alternatively, the securing material may be provided to extend over a side surface of the light guide means between the light exit end and a position away from the light exit end by a predetermined distance. In this case, it is preferred that the predetermined distance be not more than ⅓ of a distance between the light entrance end and the light exit end of the light guide means.

The securing material may be provided between the light guide means and a case forming the probe body or a case provided in the probe body.

The light guide means may be secured with the securing member between a case forming the probe body or a case provided in the probe body and a holding member that holds the acoustic wave detector. In this case, the acoustic wave detector may be attached to the holding member after the light guide member is secured with the securing member.

The invention also provides a probe comprising: an acoustic wave detector that detects at least an acoustic wave from the subject;

an optical fiber that guides light emitted from a light source to a probe body; and light guide means that guides light from a light entrance end to a light exit end, the light entrance end being optically coupled to the optical fiber and the light exit end being located in the vicinity of the acoustic wave detector, wherein the light guide means is secured in the probe body with a securing material provided at least partially around the light guide means between the light entrance end and a position away from the light entrance end by a distance h, wherein h=d/tan(θi), where d is a distance from a position where the optical fiber is coupled to the light entrance end to a side surface of the light guide means, and θi is a spread angle of light entering the light entrance end from the optical fiber.

The above-described probe may have a structure where an area of the side surface other than an area corresponding to the distance h from the light entrance end of the light guide means is covered with a layer of air.

In the probe of the invention, a securing material having a low refractive index is used as the securing material that is used to secure the light guide means in the probe body. By using a securing material that is selected such that the critical angle for total reflection at the interface between the light guide means and the securing material becomes smaller than the maximum incidence angle at which the light entering the light guide means from the optical fiber enters the interface between the light guide means and the securing material, light leakage from the light guide means to the securing material can be prevented.

DESCRIPTION OF PREFERRED EMBODIMENTS

Figure 1:
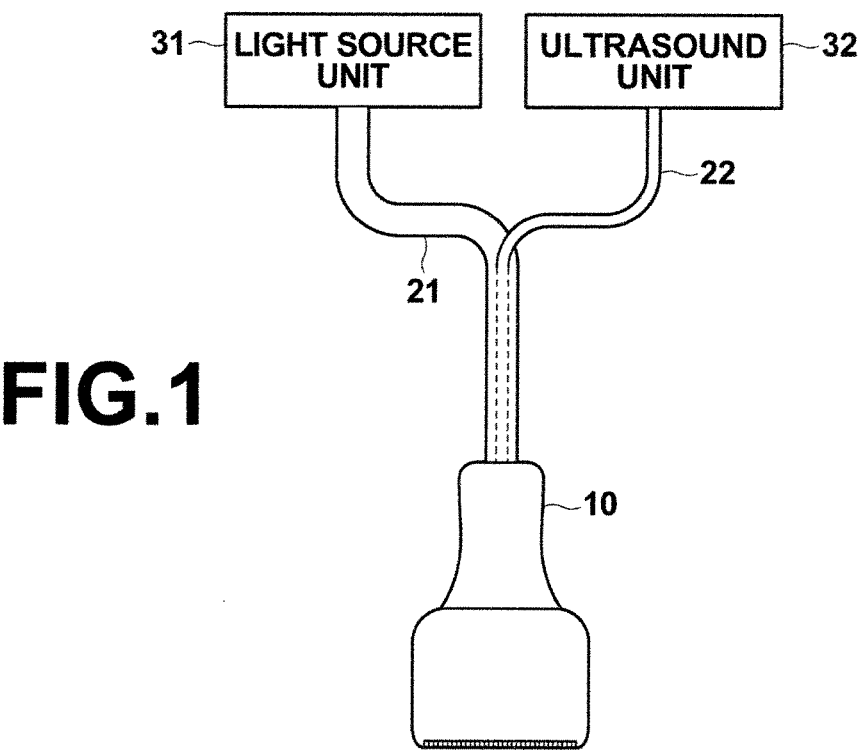
FIG. 1 is a block diagram illustrating a photoacoustic diagnostic imaging system including a probe according to a first embodiment of the invention.

Hereinafter, embodiments of the present invention will be described in detail with reference to the drawings. FIG. 1 shows a photoacoustic diagnostic imaging system including a probe according to a first embodiment of the invention. The photoacoustic diagnostic imaging system includes a probe 10, a light source unit 31, and an ultrasound unit 32. The probe 10 includes a light application section that applies light to the subject, and an acoustic wave detector that is capable of detecting an acoustic wave (ultrasound, for example) at least from the subject. The acoustic wave detector includes a plurality of ultrasound transducers, which are one-dimensionally arranged, for example.

The light source unit 31 is a laser unit that generates a pulsed laser light, for example, and generates light to be applied to the subject from the probe 10. The probe 10 is connected to the light source unit 31 via optical wiring 21. The optical wiring 21 is formed by a fiber bundle of several tens of optical fibers, for example. The pulsed laser light generated at the light source unit 31 is guided by the optical wiring 21 to the probe 10, and is applied to the subject from the light application section of the probe 10.

The ultrasound unit 32 generates a photoacoustic image based on a detection signal (ultrasound signal) of an acoustic wave detected by the probe 10. The probe 10 is connected to the ultrasound unit 32 via electric wiring 22. The ultrasound signal detected by the probe 10 is transmitted to the ultrasound unit 32 via the electric wiring 22 and is processed by the ultrasound unit 32.

Figure 2:
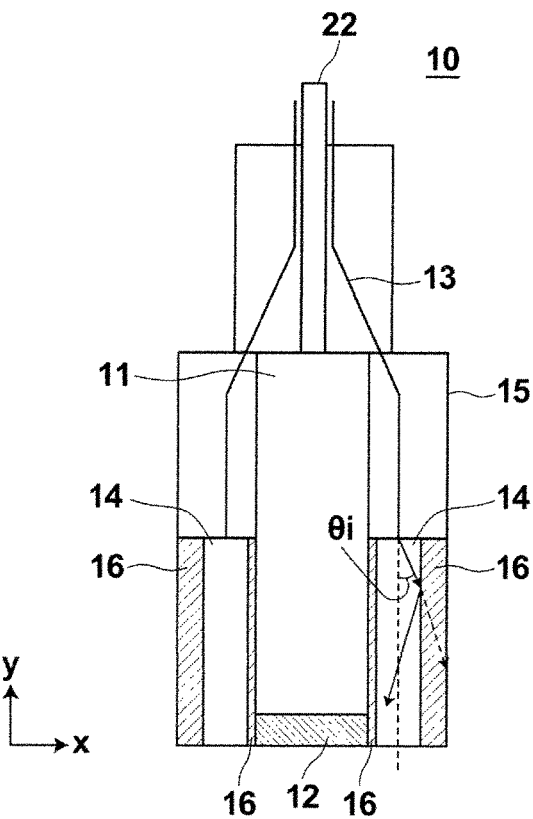
FIG. 2 is a sectional view showing a cross section in the side surface direction of the probe.

FIG. 2 shows a cross section in the side surface direction of the probe 10 viewed from a direction perpendicular to a direction in which the ultrasound transducers are arranged. The probe 10 includes electronic materials 11, optical fibers 13, and light guide plates 14. The electronic materials 11 includes ultrasound transducers 12 forming an acoustic wave detector. The ultrasound transducers 12 detect ultrasound at least from the subject. The electronic materials 11 may include, besides the ultrasound transducers 12, a pre-amplifier for amplifying the detected ultrasound, etc., for example.

The optical fibers 13 corresponds to the optical wiring 21 shown in FIG. 1, and guide light emitted from the laser light source unit 31 (FIG. 1) to the probe body. The light guide plates 14 are light guide means, each of which guides light from a light entrance end optically coupled to the optical fiber 13 to a light exit end located in the vicinity of the ultrasound transducers 12. Each optical fiber 13 is optically coupled, for example, to the center position of each light guide plate 14 in the lateral direction (x-direction) in the cross section shown in FIG. 2. The probe 10 includes at least two light guide plates 14, for example, and the two light guide plates 14 are disposed to face each other and sandwich the ultrasound transducers 12. The light guide plates 14 are made of a glass material, for example.

The light guide plates 14 are secured in the probe body by a securing material that is provided at least partially around the light guide plates 14. The securing material maybe made of a resin material, for example. The light guide plates 14 are secured in the probe body by a resin 16 that fills a space between a case forming the probe body and the electronic materials 11, for example. The resin 16 is provided to extend over the entire side surfaces (the entire surfaces in the y-direction) between the light entrance ends and the light exit ends of the light guide plates 14, for example.

As the resin 16, a resin material having a lower refractive index than that of an epoxy resin, which is a commonly-used potting agent, is used. For example, a fluorine resin material is used as the resin 16. Specifically, tetrafluoroethylene-perfluorodioxole copolymer (TFE/PDD) can be used as the resin 16. Alternatively, a low-refractive index silicone resin (having a refractive index of 1.39) or a methyl silicone resin (having a refractive index of 1.41) may be used as the resin 16. Still alternatively, in place of these resins, a fluorosilicone rubber (FE-123 having a refractive index of around 1.39, available from Shin-Etsu Chemical Co., Ltd.) may be used as the securing material.

Light entering the light entrance side of each light guide plate 14 from the end face of the optical fiber 13 travels through the light guide plate 14 with spreading at a spread angle $\theta i$ depending on the numerical aperture NA of the end face of the optical fiber 13. When the light from the optical fiber 13 enters the light entrance side of the light guide plate 14 in the normal direction, the maximum incidence angle of the light outputted from the optical fiber 13 and incident on the interface between the light guide plate 14 and the resin 16 is $90°-\theta i$. On the other hand, the critical angle (the smallest incidence angle for total reflection) is $\sin^{-1}(n2/n1) \times (180°/\pi)$, where n1 is a refractive index of the light guide plate 14, and n2 is a refractive index of the resin 16. When the critical angle is smaller than the maximum incidence angle on the interface between the light guide plate 14 and the resin 16, the light entering the light guide plate 14 travels toward the light exit end with being totally reflected.

A typical optical fiber has a numerical aperture of NA=0.23, and a spread angle $\theta i$ of the outgoing light is around 13.3°. In a case where the light guide plates 14 are made of quartz, the light guide plates has a refractive index of 1.45. As the resin 16, a fluorine resin having a refractive index n2=1.32 is used, for example. In this case, the critical angle is 65.6°. This critical angle is smaller than the maximum incidence angle of 90°−13.3°=76.7° at the interface between the light guide plate 14 and the resin 16, and therefore the light entering the light guide plate 14 from the optical fiber 13 is totally reflected at the interface between the light guide plate 14 and the resin 16.

In this embodiment, the light guide plates 14 are secured using the resin 16 having a low refractive index such that the critical angle for total reflection becomes smaller than the maximum incidence angle of the light entering the interface between each light guide plate 14 and the resin 16. Namely, a resin material having a refractive index n2 that satisfies $\sin^{-}(n2/n1) \times (180°/\pi) < 90°-\theta i$ is provided around the light guide plates 14 to secure the light guide plates 14. By using the resin material that makes the critical angle for total reflection smaller than the maximum incidence angle at which the light outputted from the optical fiber 13 enters the interface between each light guide plate 14 and the resin 16, light leakage from the light guide plates 14 can be prevented. By preventing the light leakage, light entering the light guide plates 14 can be efficiently guided to the light exit ends, thereby preventing decrease of intensity of light applied to the subject.

Figure 3:
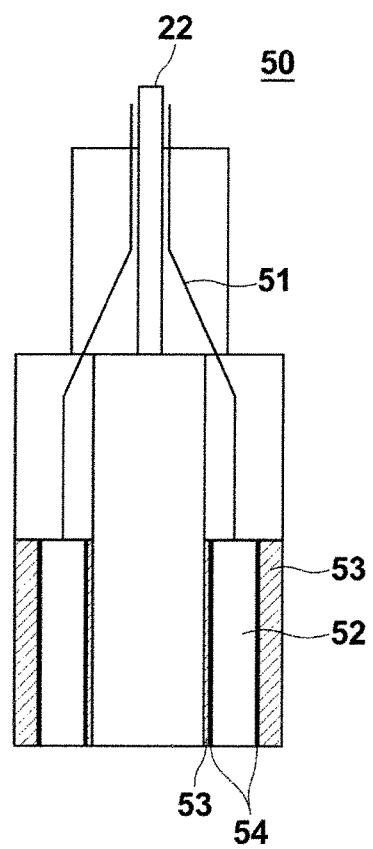
FIG. 3 is a sectional view showing a cross section in the side surface direction of a probe of a comparative example.

As a comparative example, a case where the light guide plates 14 are secured using a commonly-used potting agent is considered. FIG. 3 shows a cross section in the side surface direction of a probe of the comparative example. Light guide plates 52 are optically coupled to the optical fibers 51 to guide incoming light from the optical fibers 51 toward the subject. In the case where the light guide plates 52 are secured using, as the resin 53, an epoxy resin, which is a commonly-used potting agent and has a refractive index of around 1.42 to 1.45, the critical angle is around 78.3° to 90°. In this case, the critical angle is greater than the maximum incidence angle at the interface between each light guide plate 52 and the resin 53, resulting in light leakage. In order to prevent the light leakage, one may consider coating the interface between each light guide plate 52 and the resin 53 with a reflective film 54; however, this results in increase of the production steps and the production cost. In contrast, the embodiment of the invention can prevent the light leakage without need of a reflective coating, and thus can minimize cost increase.

Figure 4:
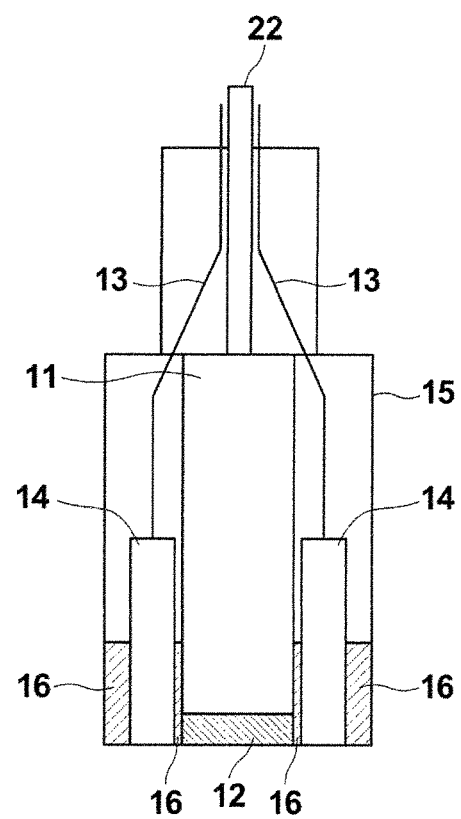
FIG. 4 is a sectional view showing a cross section in the side surface direction of a probe according to a modification of the invention.

It should be noted that the resin 16 may not necessarily be provided to extend over the entire side surfaces between the light entrance ends and the light exit ends of the light guide plates 14, and may be provided to partially extend over the side surfaces of the light guide plates 14. FIG. 4 shows a cross section in the side surface direction of a modification of the probe 10. In this example, the resin 16 is provided to extend only over the side surfaces of the light guide plates 14 between the light exit ends of the light guide plates 14 and a position away from the light exit ends by a predetermined distance. For example, the resin 16 is provided to extend over a length not greater than ½, or desirably not greater than ⅓ of the length from the light entrance ends to the light exit ends of the light guide plates 14. In this case, a necessary amount of the resin material can be reduced, although the strength for securing the light guide plates 14 decreases.

Figure 5:
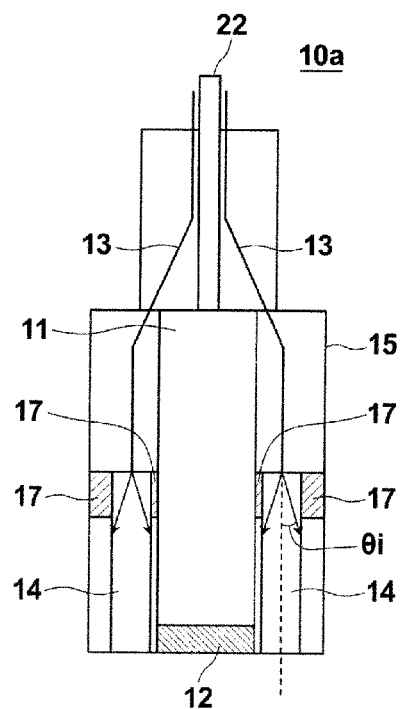
FIG. 5 is a sectional view showing a cross section in the side surface direction of a probe according to a second embodiment of the invention.

Next, a second embodiment of the invention is described. FIG. 5 shows a cross section in the side surface direction of a probe according to a second embodiment of the invention. In this embodiment, the light guide plates 14 are secured in the probe body by providing a resin 17 as the securing material at least partially around the light guide plates 14 between the light entrance ends of the light guide plates 14 and a position away from the light entrance ends by a predetermined distance h. The side surfaces of the light guide plates 14 other than the areas between the light entrance ends and the position away from the light entrance ends by the predetermined distance h are covered with a layer of air, for example.

For example, assuming that the thickness of each light guide plate 14 in the lateral direction (x-direction) of the drawing is 2×d, each optical fiber 13 is coupled to the center of each light guide plate 14 in the x-direction, and the spread angle of the light outputted from each optical fiber 13 is θi, then, light that has entered each light guide plate 14 enters the side surface (the side surface in the x-direction) of the light guide plate 14 at a position at a distance d/tan(θi) from the light entrance end. In other words, at an area between the light entrance end and the position at the distance d/tan(θi) from the light entrance end, no light outputted from the optical fiber 13 directly enters the side surface of the light guide plate 14. In this embodiment, the resin 17 is provided to extend over that area. Namely, the resin 17 is provided to extend over the area corresponding to h=d/tan(θi).

In this embodiment, the resin 17 is provided at least partially around the light guide plates 14 between the light entrance ends of the light guide plates 14 and the position away from the light entrance ends by the predetermined distance h to secure the light guide plates 14 in the probe body. By providing the resin 17 between the light entrance ends and the position at the predetermined distance defined by h=d/tan(θi) to secure the light guide plates 14, light outputted from the optical fiber 13 and entering the light guide plates 14 can be prevented from leaking out from the light guide plates 14. In this embodiment, the light outputted from the optical fiber 13 does not directly enter the resin 17. Therefore, unlike the first embodiment, it is not necessary to use a low-refractive index resin material as the resin 17. Since the areas of the light guide plates 14 that do not correspond to the predetermined distance h is covered with a layer of air, the refractive index is even smaller than the case where a fluorine resin is used, and light entering the interface between each light guide plate 14 and the layer of air is totally reflected.

Figure 6:
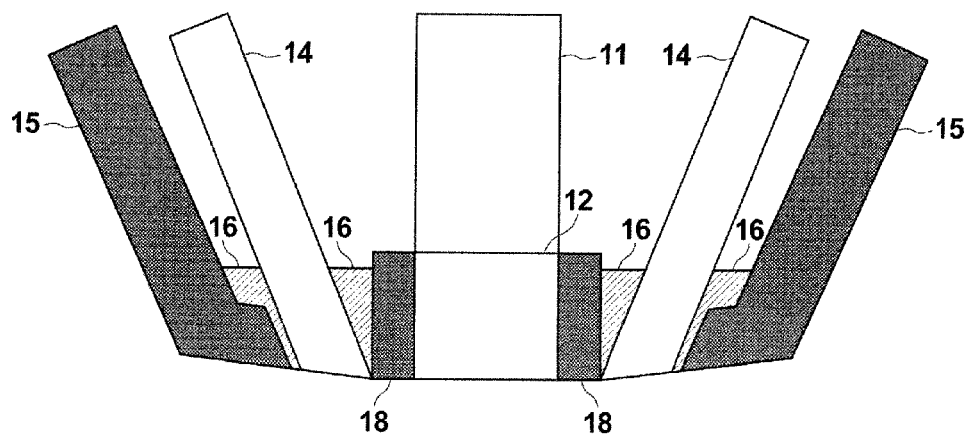
FIG. 6 is a sectional view showing a cross section of a part near the tip of a probe according to a third embodiment of the invention.

Next, a third embodiment of the invention is described. FIG. 6 shows a cross section of a part near the tip (on the ultrasound transducers side) of a probe according to the third embodiment of the invention. In this embodiment, a holding member 18 that holds the ultrasound transducers 12, which form the acoustic wave detector, is provided in the probe. The holding member 18 may be formed integrally with a case 15, which forms the outer covering, or may be formed separately from the case 15. The light guide plates 14 are secured between the case 15 and the holding member 18 with the resin 16 forming the securing member. As the resin 16, those described with respect to the first embodiment can be used.

During assembly of the probe, the resin 16 in the hot state, for example, is poured between the light guide plates 14 and the case 15 and the holding member 18, and then is hardened to secure the light guide plates 14. Thereafter, the ultrasound transducers 12 are bonded to the holding member 18. As shown in FIG. 2, in the case where the light guide plates 14 are secured between the case and the electronic materials 11 including the ultrasound transducers 12, the electronic materials 11 and the ultrasound transducers 12 are exposed to heat from the resin 16 in the hot state. In contrast, in this embodiment, the ultrasound transducers 12 can be attached to the holding member 18 after the light guide plates are secured with the resin 16. Thus, the situation where the ultrasound transducers 12, which are weak against heat, are exposed to the heat from the resin 16 in the hot state can be avoided. This allows using a material that hardens at a higher temperature as the securing material for securing the light guide plates 14. Other effects are the same as those of the first embodiment.

Figure 7:
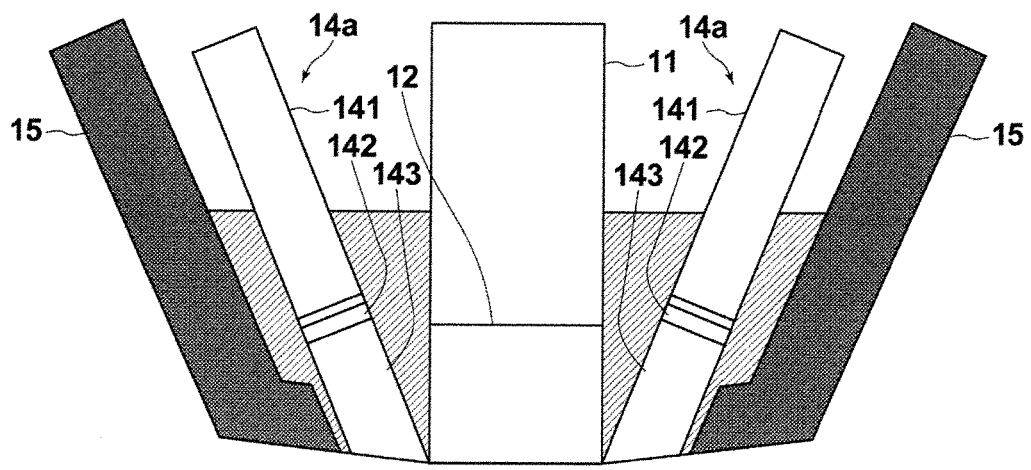
FIG. 7 is a sectional view showing a cross section of a part near the tip of a probe according to a fourth embodiment of the invention.

Next, a fourth embodiment of the invention is described. FIG. 7 shows a cross section of a part near the tip of a probe according to the fourth embodiment of the invention. In this embodiment, each light guide plate 14a includes a first light guide member 141 and a second light guide member 143. The second light guide member 143 diffuses light guided by the first light guide member 141 and guides the light to the vicinity of the ultrasound transducers 12. A gap of around 0.1 mm to 1 mm, for example, is provided between the first light guide member 141 and the second light guide member 143. The resin 16 serving as the securing member secures (parts of) the first light guide members 141 and the second light guide members 143 in the probe body.

The first light guide members 141 are made of glass, for example. High-energy laser from the light source enters the first light guide members 141, and the light entering the first light guide members 141 spreads while being guided toward the second light guide members 143. Each second light guide member 143 includes, for example, glass and a diffuser plate (light diffusing member) 142, which is disposed at the end face of the glass facing the first light guide member 141. As the diffuser plate 142, a holographic diffuser can be used, for example. The divergence angle of the diverging light entering the second light guide member 143 is further increased by the diffuser plate 142, and the diverging light is guided to the vicinity of the ultrasound transducers 12. Specifically, the divergence angle of the light is increased to $\theta d=(\theta i^2+\theta 1^2)^{1/2}$, where θ1 is a diffusion angle of the diffuser plate 142.

In this embodiment, each first light guide member 141 is made of transparent glass for receiving the incoming high-energy density laser light outputted from the optical fiber 13 (FIG. 2), and the incoming light spreads while being guided through the transparent glass. Each second light guide member 143 includes the diffuser plate 142 disposed on the light entrance side of transparent glass to further spread the incoming light from the first light guide member 141, and guides the light toward the subject. This allows minimizing a difference of light intensity between the central area and the peripheral area of the light outputted toward the subject.

In this embodiment, the light guide plates 14a are secured by providing a resin material having a refractive index n2 that satisfies $\sin^{-1}(n2/n1)\times(180°/\pi)<90°-\theta i$ around the light guide plates 14a, thereby minimizing or eliminating leakage of light from the first light guide members 141. In particular, in a case where $\sin^{-1}(n2/n3)\times(180°/\pi)<90°-\theta d$ is satisfied, where n3 is a refractive index of the second light guide members 143, leakage of light from the second light guide members 143 can be minimized or eliminated.

Figure 8:
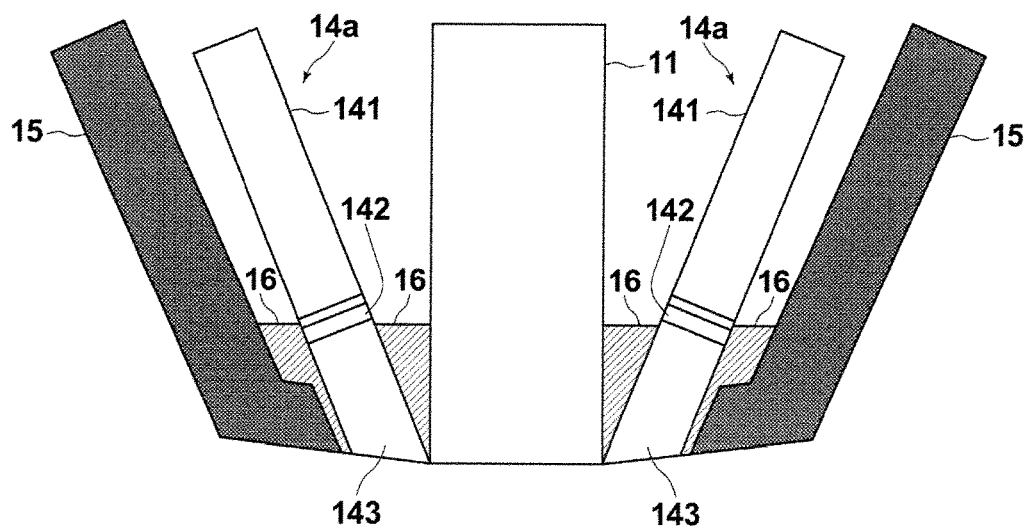
FIG. 8 is a sectional view showing a cross section of a part near the tip of a probe according to a fifth embodiment of the invention.

Next, a fifth embodiment of the invention is described. FIG. 8 shows a cross section of a tip part of a probe according to the fifth embodiment of the invention. In the above-described fourth embodiment, both the first light guide members 141 and the second light guide members 143 are secured in the probe body with the resin 16. In contrast, in this embodiment, only the second light guide members 143 of the first and second light guide members 141 and 143 are secured with the resin 16. In this embodiment, it is preferred that $\sin^{-1}(n2/n3) \times (180°/\pi) < 90° - \theta d$ (where $\theta d = (\theta i^2 + \theta 1^2)^{1/2}$) be satisfied, where n3 is a refractive index of the second light guide members 143, and $\theta 1$ is a diffusion angle of the diffuser plates 142.

In this embodiment, only the second light guide members 143 of the first and second light guide members 141 and 143 are secured with the resin 16 in the probe body. This structure allows removing only the first light guide members 141 of the first and second light guide members 141 and 143 forming the light guide plates 14a from the probe body, thereby allowing cleaning or replacement of the first light guide members 141. Further, in a case where the end faces of the second light guide members 143 on the diffuser plates 142 side are exposed above the resin 16, cleaning or replacement of the diffuser plates 142 can be performed. Other effects are the same as those of the fourth embodiment.

Figure 9:
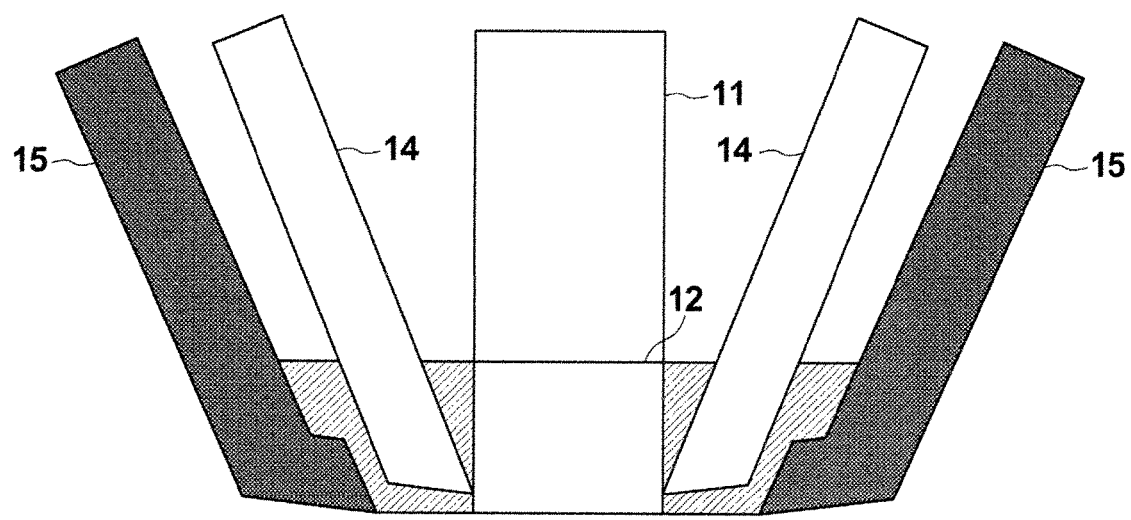
FIG. 9 is a sectional view showing a cross section of a part near the tip of a probe according to a sixth embodiment of the invention.

Next, a sixth embodiment of the invention is described. FIG. 9 shows a cross section of a part near the tip of a probe according to the sixth embodiment of the invention. The probe of this embodiment differs from the probe of the first embodiment in that the light exit ends of the light guide plates 14 are covered with the resin 16 forming the securing material. Other features are the same as those of the first embodiment.

In a case where light from the light guide plates 14 are directly applied to a living body which is the subject, a difference between the refractive index of the living body and the refractive index of the light guide plates 14 may hinder efficient application of the light to the living body. In this embodiment, light outputted from the light guide plates 14 is applied to the living body via the resin 16, which reduces the difference between the refractive index of the living body and the refractive index of the glass, thereby allowing efficient application of the light to the living body. Other effects are the same as those of the first embodiment.

It should be noted that, although the resin 16 for securing the light guide plates 14 is provided between the case 15 forming the probe body and the light guide plates 14 in the above-described embodiments, this is not intended to limit the invention. For example, another case may be provided in the probe body, and the securing member, such as a resin, may be provided between that case and the light guide plates 14 to secure the light guide plates 14 in the probe body. In the third embodiment, the securing member, such as a resin, may be provided between another case provided in the probe body and the holding member 18 (FIG. 6) to secure the light guide plates 14 in the probe body.

Further, although the light guide plates 14 in the third to sixth embodiments (FIGS. 6 to 9) are disposed obliquely so that light is also applied to an area immediately below the ultrasound transducers 12, it is not necessary to dispose the light guide plates 14 obliquely in these embodiments. On the other hand, the light guide plates 14 in the first and second embodiments (FIGS. 2, 5, etc.) may be disposed obliquely.

The above-described embodiments may be combined, as appropriate. For example, the third embodiment may be combined with the fourth embodiment such that the holding member 18 (FIG. 6) that holds the ultrasound transducers 12 is provided in the structure shown in FIG. 7, and the first light guide members 141 and the second light guide members 143 of the light guide plates 14a are secured between the case 15 and the holding member 18. The third embodiment may be combined with the fifth embodiment such that the holding member 18 (FIG. 6) that holds the ultrasound transducers 12 is provided in the structure shown in FIG. 8, and the second light guide members 143 of the light guide plates 14a are secured between the case 15 and the holding member 18.

Further, the third embodiment may be combined with the sixth embodiment such that the resin 16 covers the light exit ends of the light guide plates 14, as shown in FIG. 9, in the structure shown in FIG. 6. The fourth embodiment may be combined with the sixth embodiment such that the resin 16 covers the light exit ends of the light guide plates 14a (the light exit ends of the second light guide members 143), as shown in FIG. 9, in the structure shown in FIG. 7. The fifth embodiment may be combined with the sixth embodiment such that the resin 16 covers the light exit ends of the light guide plates 14a (the light exit ends of the second light guide members 143), as shown in FIG. 9, in the structure shown in FIG. 8.

Further, the third embodiment, the fourth embodiment and the sixth embodiment may be combined such that, in the structure shown in FIG. 7, the first light guide members 141 and the second light guide members 143 of light guide plates 14a are secured between the case 15 and the holding member 18, and the resin 16 covers the light exit ends of the light guide plates 14a (the light exit ends of the second light guide members 143), as shown in FIG. 9. The third embodiment, the fifth embodiment and the sixth embodiment may be combined such that, in the structure shown in FIG. 8, the second light guide members 143 of the light guide plates 14a are secured between the case 15 and the holding member 18, and the resin 16 covers the light exit ends of the light guide plates 14a (the light exit ends of the second light guide members 143), as shown in FIG. 9.

The present invention has been described based on the preferred embodiments. However, the probe of the invention is not limited to the probes of the above-described embodiments, and various modifications and changes made to the above-described embodiments are also within the scope of the invention.

What is claimed is:
1. A probe comprising:
   an acoustic wave detector that detects at least an acoustic wave from the subject;
   an optical fiber that guides light emitted from a light source to a probe body; and
   a light guide member that guides light from a light entrance end to a light exit end and applies light to an interior of the subject, the light entrance end being optically coupled to the optical fiber and the light exit end being located in the vicinity of the acoustic wave detector,
   wherein the light guide member is secured in the probe body with a securing material provided at least partially around the light guide member, and
   the conditional expression below is satisfied:

$$\sin^{-1}(n2/n1) \times (180°/\pi) < 90° - \theta i,$$

where n1 is a refractive index of the light guide member, n2 is a refractive index of the securing material, and θi is a spread angle of light entering the light entrance end from the optical fiber.

2. The probe as claimed in claim 1, wherein the light guide member is at least partially made of glass.

3. The probe as claimed in claim 1, wherein the securing material is made of a fluorine resin material.

4. The probe as claimed in claim 3, wherein the securing material is made of tetrafluoroethylene-perfluorodioxole copolymer.

5. The probe as claimed in claim 1, wherein the securing material is made of a fluorosilicone rubber.

6. The probe as claimed in claim 1, wherein the securing material is made of a low-refractive index silicone resin or a methyl silicone resin having a refractive index lower than the refractive index of the light guide member.

7. The probe as claimed in claim 1, wherein the light exit end of the light guide member is covered with the securing material.

8. The probe as claimed in claim 1, wherein the light guide member comprises a first light guide member that guides light emitted from the light source, and a second light guide member that diffuses and guides the light guided by the first light guide member to the vicinity of the acoustic wave detector.

9. The probe as claimed in claim 8, wherein the second light guide member comprises a light diffusing member that diffuses incoming light, the light diffusing member being disposed on the side where light from the first light guide member enters.

10. The probe as claimed in claim 9, wherein the conditional expression below is satisfied:

$$\sin^{-1}(n2/n3) \times (180°/\pi) < 90° - \theta d,$$

where n3 is a refractive index of the second light guide member, θ1 is a diffusion angle of the light diffusing member, and θd is $(\theta i^2 + \theta 1^2)^{1/2}$.

11. The probe as claimed in claim 8, wherein at least the second light guide member of the first and second light guide members is secured with the securing material.

12. The probe as claimed in claim 8, wherein only the second light guide member of the first and second light guide members is secured with the securing material.

13. The probe as claimed in claim 1, wherein the securing material is provided to extend over a side surface of the light guide member between the light entrance end and the light exit end.

14. The probe as claimed in claim 1, wherein the securing material is provided to extend over a side surface of the light guide member between the light exit end and a position away from the light exit end by a predetermined distance.

15. The probe as claimed in claim 14, wherein the predetermined distance is not more than ⅓ of a distance between the light entrance end and the light exit end.

16. The probe as claimed in claim 1, wherein the securing material is provided between the light guide member and a case forming the probe body or a case provided in the probe body.

17. The probe as claimed in claim 1, wherein the light guide member is secured with the securing member between a case forming the probe body or a case provided in the probe body and a holding member that holds the acoustic wave detector.

18. The probe as claimed in claim 17, wherein the acoustic wave detector is attached to the holding member after the light guide member is secured with the securing member.

19. A probe comprising:
an acoustic wave detector that detects at least an acoustic wave from the subject;
an optical fiber that guides light emitted from a light source to a probe body; and
a light guide member that guides light from a light entrance end to a light exit end and applies light to an interior of the subject, the light entrance end being optically coupled to the optical fiber and the light exit end being located in the vicinity of the acoustic wave detector,
wherein the light guide member is secured in the probe body with a securing material provided at least partially around the light guide member between the light entrance end and a position away from the light entrance end by a distance h, wherein h=d/tan(θi), where d is a distance from a position where the optical fiber is coupled to the light entrance end to a side surface of the light guide member, and θi is a spread angle of light entering the light entrance end from the optical fiber.

20. The probe as claimed in claim 19, wherein an area of the side surface other than an area corresponding to the distance h from the light entrance end of the light guide member is covered with a layer of air.

* * * * *